United States Patent [19]

Schlaefke et al.

[11] Patent Number: 4,813,427

[45] Date of Patent: Mar. 21, 1989

[54] APPARATUS AND METHOD FOR PREVENTING HYPOXIC DAMAGE

[75] Inventors: Marianne E. Schlaefke, Bochum; Joachim Hopmeier, Freiburg, both of Fed. Rep. of Germany

[73] Assignee: Hellige GmbH, Freiburg, Fed. Rep. of Germany

[21] Appl. No.: 15,635

[22] Filed: Feb. 17, 1987

[30] Foreign Application Priority Data

Feb. 17, 1986 [DE] Fed. Rep. of Germany ....... 3604986

[51] Int. Cl.$^4$ .................................................. A61B 5/08
[52] U.S. Cl. ...................................... 128/671; 128/716; 128/721
[58] Field of Search ................................ 128/670–671, 128/716, 719, 721–723, 687, 637, 736, 664–666

[56] References Cited

U.S. PATENT DOCUMENTS

| | | | |
|---|---|---|---|
| 3,572,317 | 3/1971 | Wade | 128/671 |
| 3,802,417 | 4/1974 | Lang | 128/716 |
| 4,366,821 | 1/1983 | Wittmaier | 128/719 |
| 4,414,982 | 11/1983 | Durkan | 128/716 |
| 4,580,575 | 4/1986 | Birnbaum et al. | 128/671 |
| 4,619,270 | 10/1986 | Margolis et al. | 128/721 |
| 4,694,839 | 9/1987 | Timme | 128/721 |

OTHER PUBLICATIONS

Schlaefke et al., "Loss of Central Chemosensitivity, Exper. Studies on a Clin. Problem", *Adv. Physiol Sci. vol. 10*, pp. 609–616.

Schlaefke et al., "Training of Central Chemosensitivity in Infants with Sleep Apnea", *Central Neurone Environment*, pp. 75–81.

*Primary Examiner*—Kyle L. Howell
*Assistant Examiner*—Angela D. Sykes
*Attorney, Agent, or Firm*—Edward J. Whitfield

[57] ABSTRACT

Disclosed are apparatus and method for preventing hypoxic damage, relieving respiratory difficulties and conditioning breathing reflexes in a living human body. More particularly, at least one sensory stimulus is imparted to the body in response to a deviation from at least one adjustable physiological variable followed sequentially by delivery of a respiration restoring gas to the vicinity of the nose and mouth of the body.

9 Claims, 2 Drawing Sheets

APPARATUS AND METHOD FOR PREVENTING HYPOXIC DAMAGE

FIELD OF THE INVENTION

The invention relates to apparatus and method for preventing hypoxic damage and for relieving breathing difficulties.

BACKGROUND OF THE INVENTION

In healthy people, hypoxia results in a marked accentuation of breathing. If the oxygen content in the blood falls below a critical value, serious effects occur with persistent hypoxia, for example metabolic derangement owing to production of lactic acid, tissue acidosis, cell damage. The brain and heart are at particular risk. The possible consequences of cerebral impairment are neuromuscular coordination disorders, a diminution in judgment, visual disturbances, sweats, collapse and unconsciousness, increase in cerebral pressure, convulsions and loss of brain tissue. The cardiac disorders which could result are, for example, ventricular extrasystoles, ventricular fibrillation, cor pulmonale (right ventricular strain) and changes in the walls of pulmonary vessels.

Hypoxic states are frequently the consequence of breathing difficulties. A deficiency of respiratory drive owing to impairment of the regulatory systems in the central nervous system is often evident only under resting conditions. Thus, as is known, breathing difficulties in premature babies resulting from immature brain structures, and breathing difficulties in early childhood may cause what is called sudden infant death syndrome (SIDS) in the first few months of life. The hazard in this context is prolonged and often unrecognized hypoxic states during sleep, with a pathological lack of an accentuation of breathing, so that damage in the central and autonomic nervous systems and in the cardiopulmonary system can arise.

The use of ventilation equipment for the temporary treatment of breathing difficulties is known. Also known is the electrical stimulation of phrenic nerves for artificial initiation of breathing movements. Likewise known is the pharmacological treatment of difficulties of this type. In the context of therapy of breathing difficulties in premature babies, oxygen therapy, for example, an oxygen tent, has frequently been used. However, the known oxygen therapy of premature babies may result in blinding and damage to the lungs with impairment of gas exchange.

Where patients with central breathing difficulties are artificially ventilated using ventilating equipment, although the gas exchange, which is absolutely necessary for life is maintained, the therapeutic measures for restoring spontaneous breathing are inadequate. It is known that when prolonged artificial ventilation is used, patients may lose, at least temporarily, the ability to breathe spontaneously.

It has been found that electrical stimulation of the phrenic nerves could cause irreversible damage to the nerves, and, frequently, uncoordinated breathing movements, so that a tracheotomy is necessary to avert airway blockage.

Pharmacological therapy is often unsuccessful or only temporarily successful, and it may result in drug dependence and may have drastic adverse effects on sleeping behavior.

The known treatment methods described herein frequently have the disadvantage that the patient loses the ability to breathe spontaneously because the breathing reflexes are not trained. Nor is there promotion of maturation of the respiratory system which in premature babies is frequently insufficiently advanced.

Given the lack of suitable therapeutic approaches, to date people have been confined to using apnoea monitors, in particular as equipment in the homes of babies at risk from sudden infant death syndrome (SIDS). When breathing is interrupted, the monitor generates a visible or audible alarm which wakes the sleeper. It is disadvantageous that, with this action which is exclusively for rescue, there is neither elimination of the danger of chronic hypoxia nor support for the maturation of the breathing reflex.

Because of the dangers and side effects of the current therapeutic options which have been discussed, as a rule only serious breathing difficulties are treated. On the other hand, untreated breathing difficulties can result in fatal disorders, for example, SIDS.

SUMMARY OF THE INVENTION

This invention, in one aspect, provides apparatus for detecting a breathing or respiratory disorder and sequentially delivering in response to detection of such disorder a sensory stimulus and respiration restoring gas. Also, use of the apparatus provides long-term conditioning of breathing reflexes. More particularly, this invention provides apparatus for preventing hypoxic damage and restoring normal respiration to a living human body comprising means associated with said body for monitoring and measuring at least one physiological variable within adjustable limits; first means associated with and actuated by said measuring and monitoring means whereby when a physiological variable deviates from said predetermined limits, at least one sensory stimulus is imparted to said body; and second means associated with said measuring and monitoring means whereby when a physiological variable deviates from said adjustable limits and after an adjustable interval of time following impartation of said sensory stimulus, a respiration restoring gas is delivered for an adjustable time period to the vicinity of the nose and mouth of said body. The sequence of imparting sensory stimulus and delivering respiration restoring gas continues until the physiological variable is within its adjustable limits.

This invention, in another aspect, provides a method for detecting a breathing or respiratory disorder, restoring normal respiration, and conditioning breathing reflexes. More particularly, a method is provided for preventing hypoxic damage and restoring normal respiration by the steps of selecting at least one of the body's physiological variables and adjusting limits of such variable; measuring and monitoring such physiological variable; imparting at least one sensory stimulus to the body for an adjustable period of time in response to a deviation of the physiological variable from said adjustable limits; delivering respiration restoring gas to the vicinity of the nose and mouth of said body for an adjustable time period after lapse of an adjustable interval of time following impartation of said sensory stimulus; and sequentially continuing impartion of sensory stimulus, and delivery of respiration restoring gas until the physiological variable is within its adjustable limits.

THE DRAWINGS

The invention is illustrated in detail below, with reference to the exemplary embodiment depicted in the drawings, wherein.

DESCRIPTION OF THE INVENTION

Figure 1:
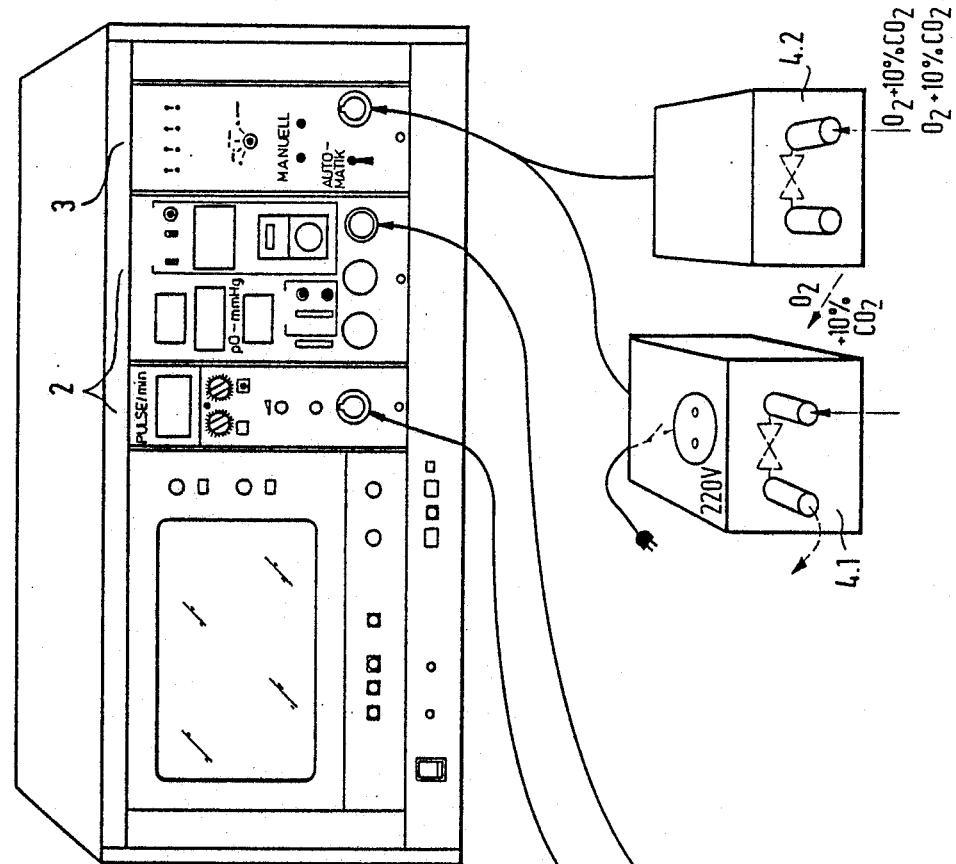
FIG. 1 shows diagrammatically apparatus comprising the therapeutic system according to the invention.
Figure 1:
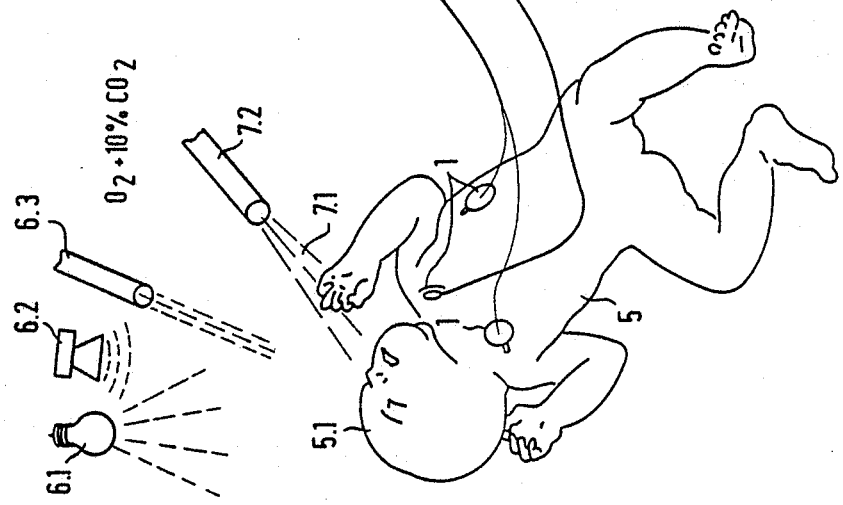

As shown in FIG. 1, the apparatus according to the invention monitors and measures, via sensors 1, e.g., polarographic electrodes, which are attached to the skin of the patient 5, physiological variables associated with breathing or respiration and/or the oxygen supply to the body tissue. Monitoring is carried out, by appropriate measuring instruments 2, for example of the breathing rate, the depth of breathing, the heart rate, the pulse rate or the content of oxygen or carbon dioxide in the blood. The production of perspiration or the cerebral pressure may also be important variables to be measured.

The apparatus, 2, may be any instrument or combination of conventional commercially available instruments typically used to measure and monitor physiological variables in the human body. Some examples of such apparatus include a heart rate monitor (e.g., Hellige Servomed ® No. 23605302); a blood oxygen tension monitor (e.g., Hellige Servomed ® No. 23606501); a respiration monitor (e.g., Hellige Servomed ® No. 23606102); a blood carbon dioxide monitor (e.g., Hellige Servomed ® No. 23606601); a temperature monitor (e.g., Hellige Servomed ® No. 23605902); a blood oxygen saturation monitor (e.g., Ohmeda Biox 3700); and the like.

The measuring apparatus 2 is provided with adjustable alarm devices so that an internal alarm is triggered if the measurement is above the upper adjustable physiological limit or below the lower adjustable physiological limit.

The alarms determined by the measuring apparatus 2 are "preliminary alarms" and result in therapy-initiating measures only in particular special cases. The combination of measuring apparatus 2 most suitable for a particular patient will be established by a meticulous preliminary examination of the patient.

The alarm signals are passed from the measuring apparatus 2 to an alarm-combination device 3 with which the individual preliminary alarms are combined to produce a therapy-initiating event. The output signals from the alarm-combination device 3 actuate switching devices 4.1 and 4.2.

Although a single switching device could be used to actuate both the unspecific breathing initiation stimulus and the specific breathing stimulus, for safety reasons two separate switching devices as illustrated are preferred. The switching devices 4.1 and 4.2 are of conventional construction, switching device 4.1 comprising a housing containing a relay (e.g., Siemens V23016) for use with 112/220 volt power supply and maximum current of about 1.6 amperes to actuate the sensory stimulus and may include a magnetic valve (e.g., Pneutronics No. 11161BB) for controlling air flow with a maximum over-pressure of about 1.7 bar. Switching device 4.1 is preferably provided with a separate power line. Switching device 4.2 is similar to 4.1 and comprises a housing containing a magnetic valve (e.g., Pneutronics No. 11161BB) for controlling respiratory gas flow at a maximum over-pressure of about 1.0 bar. The magnetic valve is not lubricated and contains no oxygen sensitive internal parts or bearings, and is provided with oxygen resistant silicon connecting tubes for connection with the housing and respiratory gas feed and delivery lines. Also, the housing is provided with lateral ventilation bores to prevent accumulation of oxygen rich gas in the housing in the event of any leakage. The power supplied to switching device 4.2 is, of course, sufficiently low so as to not create any explosive hazard.

Switching device 4.1 controls that part of a sequence of actions 8 (compare FIG. 2) which corresponds to an unspecific breathing-initiation or sensory stimulus 8.1. The unspecific breathing-initiation stimulus 8.1 can be composed of various sensory stimuli, for example of light, sound, motion or olfactory stimuli or stimuli which can be felt through the skin, such as impinging gas, tickling or the action of heat/cold.

Several stimulating devices 6.1 to 6.3 are fixed near the head 5.1 of the patient 5, and through these the unspecific breathing-initiation or sensory stimulus 8.1 is imparted to the patient 5. Examples of suitable devices for imparting sensory stimulus 6 are light bulbs, flashlamps, loudspeakers, tubes with air flowing out, or the like.

The unspecific breathing-initiation stimulus 8.1 can, of course, be composed of a combination of several sensory stimuli, for example of a light stimulus and a sound stimulus. The various sensory stimuli can be imparted to the patient 5 synchronously or sequentially. The unspecific breathing-initiation stimulus typically lasts about 0.2 to 5 seconds, preferably 0.5 to 2 seconds. Another part of the sequence of actions 8, namely the specific breathing stimulus 8.3, is imparted to the patient via the switching device 4.2. During the specific breathing stimulus 8.3 a special respiratory gas mixture 7.1, which contains higher concentration(s) of carbon dioxide and/or oxygen or other suitable substances than normal ambient air, is impinged by means of a tube 7.2 in the region of the nose and mouth of the patient 5. The specific breathing stimulus 8.3 typically lasts about 0.2 to 5 seconds, preferably 0.5 to 2.0 seconds.

The interval 8.2 between the unspecific breathing-initiation stimulus 8.1 and the specific breathing stimulus 8.3 within a single sequence of actions 8 typically lasts 0.2 to 5 seconds, preferably 0.3 to 0.8 seconds.

In the case of breathing difficulties with a deficient carbon dioxide respiratory drive, no accentuation of breathing is found despite a high hydrogen ion concentration. The central chemoreflex responsible for this can, however, be trained with specific breathing stimuli, for example by admixture of carbon dioxide to the respiratory gas with, preferably, a simultaneous increase in the oxygen concentration. This promotes chemosensitivity in the central nervous system. It is particularly suitable, for example, if the patient inhales a gas mixture containing about 2% carbon dioxide and 40 to 98% oxygen, in addition to nitrogen, and if, shortly before or simultaneously with the provision of the stream of respiratory gas, an unspecific breathing-initiation stimulus such as, for example, a flash of light is triggered, since it promotes respiratory drive.

The interval 9 between two consecutive sequences of actions 8 lasts 2 to 30 seconds, preferably 5 to 15 seconds.

Figure 2:
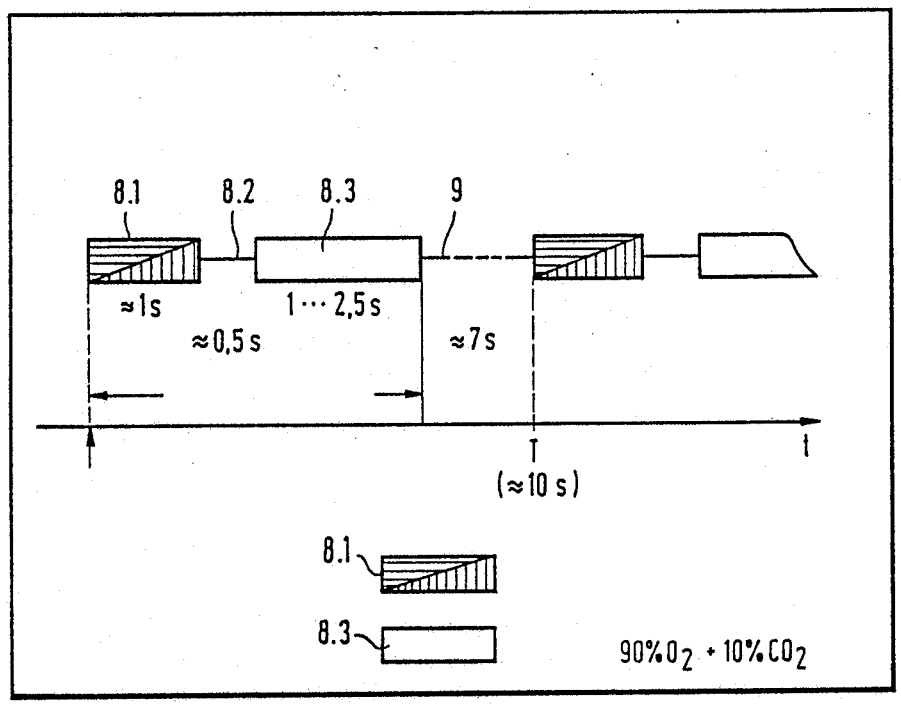
FIG. 2 shows the time-course of the unspecific breathing-initiation or sensory stimulation and of the specific breathing stimulation.

The time-course of a sequence of actions 8, composed of the unspecific breathing-initiation stimulus 8.1 and the specific breathing stimulus 8.3 and including the pause 8.2 between the two stimuli, together with the pause 9 between two consecutive sequences of actions 8, is depicted in detail in FIG. 2.

Where the improvement in breathing is inadequate, especially where the improvement in oxygen is insufficient, the sequence of actions 8, composed of breathing-initiation stimulus 8.1 and, where appropriate, specific breathing stimulus 8.3, is repeated and is not terminated until the therapy-initiating alarm has been cancelled.

Figure 3:
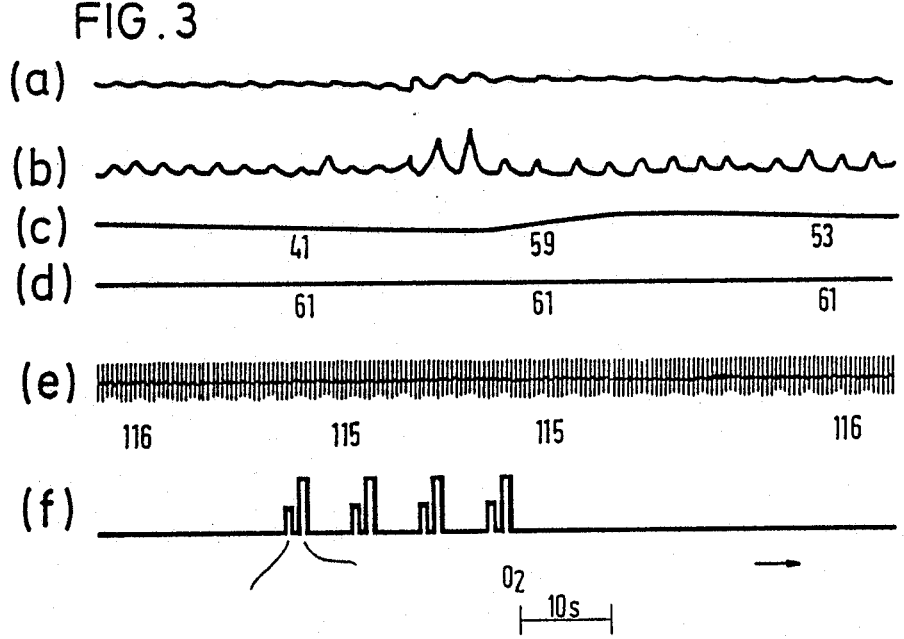
FIG. 3 shows the time-related display of measured physiological variables, in particular of respiratory activity, in a neonate suffering from breathing difficulties.

FIG. 3 shows the time-course of various measured physiological variables in an infant. The two upper signal tracings (a) and (b) illustrate the thoracic and abdominal breathing movements respectively. Signal tracings (c) and (d) show the partial pressures of oxygen and carbon dioxide ($tcpO_2$ and $tcpCO_2$ respectively) measured transcutaneously. Tracing (e) corresponds to the ECG or the change in heart rate. Diagram (f) shows the sequence of actions triggered by the equipment according to the invention, there being a total of four sequences of actions triggered at a time interval of about 10 seconds with a preceding unspecific breathing-initiation stimulus and a subsequent, after a brief pause, specific breathing stimulus. As can be seen, the first two sequences of actions (stimuli) have not yet resulted in the desired response, in particular with the unsatisfactory breathing movements in the abdominal area. However, the third sequence of actions greatly stimulates the breathing activity, which subsequently converts to the normal state. At the same time, the $tcpO_2$ rises to a normal plateau level.

In a further development of the invention, the apparatus includes means which, when the result of therapy is persistently inadequate, automatically modifies, and suits to the conditions of the individual patient's disorder, the sequence of actions 8 so that breathing is improved. It is also possible for assessment of the result of therapy which has actually been achieved or is to be expected in the long-term with regard to an adequate blood oxygen content and spontaneous breathing, to evaluate additional measured physiological variables which are not necessarily monitored for generation of the therapy-initiating alarm. For example, the instantaneous blood oxygen content may be an appropriate alarm variable, whereas the blood carbon dioxide content, which is measured after a time-lag for example, may have prognostic significance for the result of treatment which is to be expected.

As discussed hereinabove, the apparatus according to the invention enables detection of breathing difficulties and, moreover, effects a rapid improvement in the blood oxygen content and conditions the breathing reflexes. Long-term success of therapy can be achieved by, for example, facilitating the central chemoreflex which is controlled by carbon dioxide content. With the invention apparatus the body learns to break out of the vicious circle of its pathological breathing and to lose its dependence on the therapy in the long-term.

The apparatus is suitable for use for the respiratory distress syndrome of premature babies, in the area of neonatology for training the disturbances, caused by, for example, perinatal hypoxia, of the central nervous system with respiratory insufficiency, for the prophylaxis of SIDS when the blood oxygen content decreases during sleep in the first year of life, for use in patients on ventilators, for example in the weaning-off phase, for the sleep apnoea syndrome of adults, and in the area of neurosurgery for transient central breathing difficulties following surgery and trauma.

The apparatus according to the invention measures at least one physiological variable which is connected with breathing or the tissue oxygen supply, and when the result is above or below limits, initiates therapeutic measures. There is monitoring of, for example, the breathing rate, the depth of breathing, the heart or pulse rate, or the oxygen or carbon dioxide content of the blood. The signs which can be observed in connection with hypoxia, such as perspiration or a changed cerebral pressure can provide further important variables for measurement.

The specific combination of measuring instruments most suited for measuring physiological variables for the particular patient is established at a meticulous preliminary examination of the patient. Use is preferably made of those combinations of parameters which are the clearest signal of the clinical picture and can be measured with the greatest reliability, and where possible with little sleep disturbance. The preliminary examination of the patient may show that it is sufficient to monitor the heart rate for pathological intrusions, for example periods of bradycardia indicating excessively long pauses between breaths. Other patients have periods of bradycardia unassociated with pauses between breaths. False alarms can then be suppressed by monitoring additional measured variables, for example the breathing rate. For every variable, when the results are above or below individual limits, preliminary alarms are generated, which need not be evident from the outside but whose suitable logical combination represents a therapy-initiating event. There are many possible combinations of the individual preliminary alarms, which result from the physiological variables influenced by breathing, to bring about the therapy-initiating event. The variables to be monitored and the mode of combination of their preliminary alarms are selected to suit the patient and his clinical picture with the aim of good therapeutic results and minimal false-positive and false-negative therapy-initiating events. For example, in babies with the sleep apnoea syndrome, simultaneous monitoring of the heart rate and of the partial pressure of oxygen in the blood, measured transcutaneously, when every preliminary alarm itself initiates the therapeutic measures, is of proven use.

In order to achieve immediate improvement in the blood oxygen content, when the therapy-initiating event takes place there is first of all stimulation or, where there is respiratory arrest, "triggering" of the respiratory center without, in generally, waking the patient. Suitable and preferred for this "breathing-initiation action" are unspecific sensory stimuli, such as light, sound or olfactory stimuli or stimuli detectable in the skin, by which means the respiratory depression associated with mechanical ventilation is avoided. It is also possible to trigger synchronous or metachronous breathing-initiation stimuli of various types. It is particularly beneficial to impinge on the patient's face a brief stream of respiratory gas which may, advantageously, contain a higher oxygen concentration. A puff of air, for example, in the region of the nose and mouth, stimulates the trigeminal nerve whose activity influences the basic activity of the respiratory center in the direction of improving respiratory drive. The inhalation triggered by a breathing-initiation stimulus is more effective when respiratory gas having a higher oxygen concentration is offered. It is also possible briefly to introduce oxygen directly into the nose, in which case, despite adequate oxygenation, premature babies now do not normally suffer oxygen-induced damage.

Although the invention has been described herein in considerable detail and with reference to preferred embodiments thereof, many variations may be made therein without departing from the spirit and scope thereof as defined by the appended claims.

We claim:

1. Apparatus for preventing hypoxic damage and restoring normal respiration in a living human body said apparatus comprising:
   (a) means associated with said body for measuring and monitoring at least one physiological variable within adjustable limits;
   (b) first means associated with and actuated by said measuring and monitoring means whereby when a physiological variable deviates from said adjustable limits, at least one sensory stimulus is imparted to said body for an adjustable time period; and
   (c) second means associated with and actuated by said measuring and monitoring means whereby when a physiological variable deviates from said adjustable limits and after an adjustable time interval following impartation of said sensory stimulus, a respiration restoring gas is delivered, for an adjustable time period, to the vicinity of the nose and mouth of said body.

2. The apparatus of claim 1 wherein the measuring and monitoring means is selected from a heart rate monitor, a blood oxygen tension monitor, a respiration monitor, a blood carbon dioxide monitor, a temperature monitor, a blood oxygen saturation monitor or combinations of such monitors.

3. The apparatus of claim 1 wherein said first means comprises electrical switching means for actuating and imparting said sensory stimulus in response to an electrical signal from said measuring and monitoring means.

4. The apparatus of claim 3 further including magnetic valve means.

5. The apparatus of claim 1 wherein said second means comprises a magnetic valve means for delivering respiration restoring gas in response to an electrical signal from said measuring and monitoring means.

6. A method for detecting a respiratory disorder, restoring normal respiration and conditioning respiratory reflexes in a living human body said method comprising:
   (a) measuring and monitoring at least one selectable physiological variable of said body and adjusting limits of such variable;
   (b) detecting a variance from said adjustable limits of said selected physiological variable;
   (c) imparting at least one sensory stimulus to the body for an adjustable period of time in response to detecting said variance;
   (d) delivering respiration restoring gas to the vicinity of the nose and mouth of said body for an adjustable period of time after an adjustable interval of time following impartation of said sensory stimulus; and repeating the sequence of imparting sensory stimulus and delivering respiration restoring gas until the physiological variable is within said adjustable limits.

7. The method of claim 6 wherein the physiological variable measured and monitored is selected from heart rate, blood oxygen tension, respiration rate, blood carbon dioxide content, temperature, blood oxygen saturation and the like or combinations thereof.

8. The method of claim 6 wherein the sensory stimulus is imparted for a period of from 0.2 to 5 seconds, the respiration restoring gas is delivered for a period of from 0.2 to 5 seconds, and the interval between imparting sensory stimulus and delivering respiration restoring gas is from about 0.2 to 5 seconds.

9. The method of claim 8 wherein the sensory stimulus is imparted for from 0.5 to 2 seconds, the respiration restoring gas is delivered for from 0.5 to 2 seconds, and the interval therebetween is from 0.3 to 0.8 seconds.

* * * * *